United States Patent [19]
Abitbol

[11] Patent Number: 6,147,751
[45] Date of Patent: Nov. 14, 2000

[54] LENS REFRACTOMETER

[75] Inventor: Mordechai Abitbol, Jerusalem, Israel

[73] Assignee: Visionix Ltd., Jerusalem, Israel

[21] Appl. No.: 09/379,942

[22] Filed: Aug. 24, 1999

[30] Foreign Application Priority Data

Oct. 21, 1998 [IL] Israel .......................................... 126693

[51] Int. Cl.$^7$ .............................. G01N 21/41; G02B 5/20
[52] U.S. Cl. ............................ 356/128; 356/128; 356/124; 356/125; 359/177; 359/197; 359/362; 359/642
[58] Field of Search ...................... 356/124–128; 359/197, 177, 642, 362

[56] References Cited

U.S. PATENT DOCUMENTS

| | | | |
|---|---|---|---|
| 3,985,445 | 10/1976 | Tagnon | 356/125 |
| 5,151,752 | 9/1992 | Oono | 356/128 |
| 5,847,819 | 12/1998 | Yanagi | 356/124 |

FOREIGN PATENT DOCUMENTS

| | | | |
|---|---|---|---|
| 2618552 | 1/1989 | France | |
| 3724001 | 2/1989 | Germany | |
| 1460158 | 12/1976 | United Kingdom | |

OTHER PUBLICATIONS

Derwent Abstract of DE 37 24 001 of Feb. 2, 1989.
Derwent Abstract of FR 2618552 of Jan. 27, 1989.

*Primary Examiner*—Robert H. Kim
*Assistant Examiner*—Delma R. Flores Ruiz
*Attorney, Agent, or Firm*—Ladas & Parry

[57] ABSTRACT

A refractometer and a method for measuring the refractive index of a lens, wherein a thin insert in the form of a pad of a flexible transparent material attached to a rigid transparent sheet, is lightly pressed onto a surface of the lens under test, such that the pad surface effectively acquires the same profile as the lens surface. The focal length or power of the lens is first measured without the insert, and the measurement is then repeated with the insert positioned first in contact with one surface of the lens, and then in contact with the other surface. The use of equations derived from the classical lens formula then enables the refractive index of the lens to be easily and quickly determined. The apparatus and method also enables the measurement of the refractive index of lenses of low power.

21 Claims, 3 Drawing Sheets

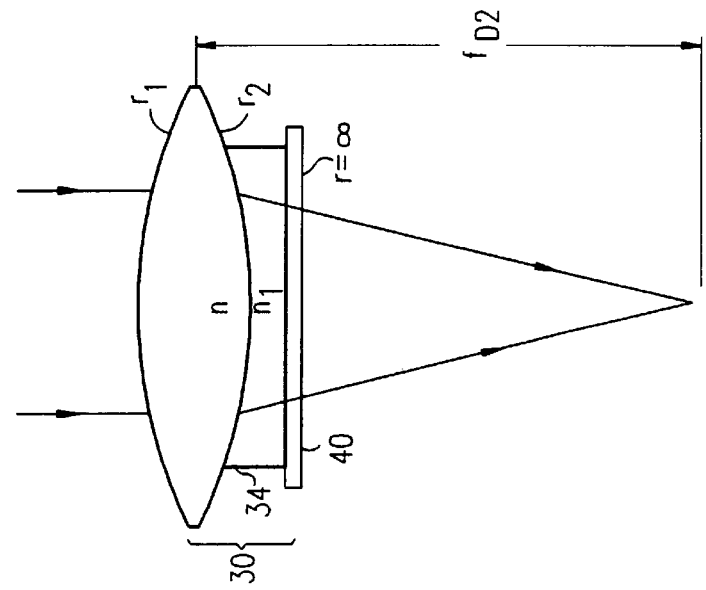
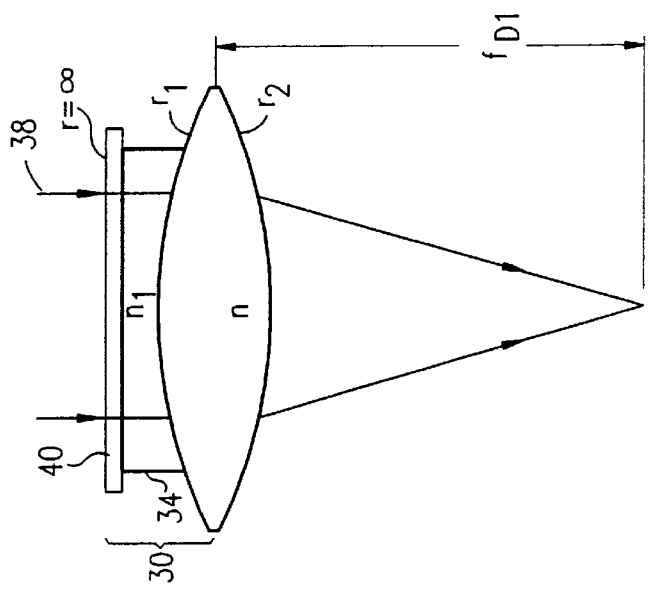
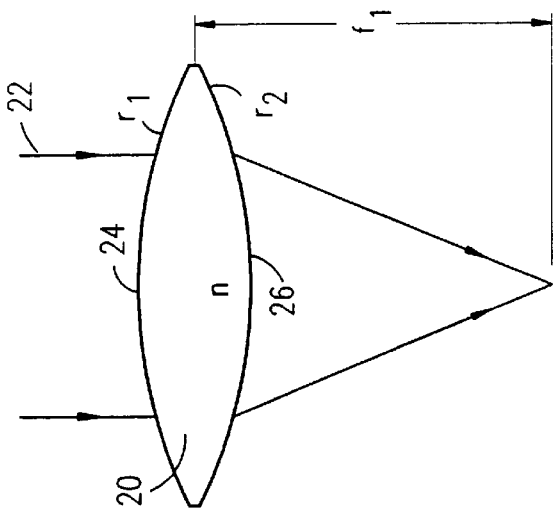

LENS REFRACTOMETER

FIELD OF THE INVENTION

The present invention relates to the field of instrumentation for measuring the refractive index of lenses, especially ophthalmic lenses.

BACKGROUND OF THE INVENTION

There exist a number of methods for determining the refractive index of optical materials. If the material is in the form of a well-defined geometric shape with straight sides, such as a block or a prism, and the sides are polished, then a classic method is to measure the critical angle of a ray of light refracted into the block. The refractive index of the material is then related to the critical angle by means of the equation $\sin \theta_c = 1/n$, where n is the refractive index to be measured, and $\theta_c$ is the critical angle. If the material is in the form of a block of known thickness, then a traveling microscope can be used to measure the optical thickness, which is known to be $1/n$ times the actual measured thickness. The refractive index n can thus be determined.

In the characterization of lenses, it is often necessary to determine the refractive index of the lens material. The above methods cannot be used for a lens, or for any irregularly shaped object, since the material to be measured does not have a well-defined straight-sided geometric shape. Early methods for lenses and other irregular-shaped objects include that of immersing the object into a known mixture of fluids, and adjusting the mixture components until the object seems to disappear, which occurs when it has the same refractive index as the fluid. A knowledge of the fluid composition enables its refractive index to be determined from known tables. Fluids suitable for this method, include organic fluids such as carbon disulfide, benzene and nitrobenzene.

For a lens, another method is to measure its focal length by one of the classical methods, and to mechanically measure the radii of curvature of its two surfaces using a spherometer. The refractive index n of the lens material can then be calculated using the well-known lens formula:

$$1/f = (n-1)[1/r_1 - 1/r_2] \quad (1)$$

where f is the focal length, and $r_1$ and $r_2$ are the radii of curvature of the surfaces.

This method cannot be used in situations where the use of a spherometer is inconvenient, or, if mechanical contact could damage the lens surface, or, if the lens material is not rigid enough to withstand mechanically deformation during a spherometric measurement. All of these situations may be likely in the case of very small lenses such as ophthalmic contact lenses.

More modem methods have been proposed using high speed electronic circuits and optoelectronic generators, wherein the time of flight of a beam of light over a particular path is compared, with and without a lens in the beam path. The slight delay caused by the increased optical path length through the lens, enables the refractive index of the lens material to be obtained. Such apparatus is very expensive, and thus unsuitable for widespread use.

An alternative and cheaper non-contact method is that of immersing the lens in a liquid bath, contained in an immersion cell, and measuring its focal length with and without the liquid, using a focimeter or lens power meter. Applying the lens equation (1) for the two cases, once with the multiplicand (n−1) when the lens is unimmersed, where the "1" approximates the refractive index of the air surrounding the lens, and once with the multiplicand (n−$n_1$), where $n_1$ is the refractive index of the liquid in which the lens is immersed, it is possible to calculate the unknown refractive index. The result of this calculation is that $$f_2/f_1 = (n-1)/(n-n_1) \quad (2)$$

where $f_2$ and $f_1$ are the measured focal lengths with and without the immersion liquid. Using either a manual focimeter, or an automatic power meter, the unknown refractive index n of the lens can be easily obtained. This method has been widely used in the ophthalmic industry for many years, despite the inconvenience of handling and drying the lens after fluid immersion. In some cases, immersion of the lens may be forbidden, and this method cannot then be used.

In German Patent No. 3724001 to W. Vieweg, hereby incorporated by reference, there is described a variation of the fluid immersion method, wherein the two lens surfaces are sandwiched between two layers of a soft flexible transparent plastic material, such as RTV, which effectively "immerse" the lens in the plastic medium during measurement. This method uses exactly the same calculations as the classical fluid immersion method, the end result of which is shown in equation (2) above, but has an advantage of greater convenience since no fluids are involved. The layers of the soft flexible transparent plastic material are in the form of pads, with the side remote from that which contacts the lens surface being attached to a flat rigid transparent sheet of glass or plastic material, through which the light enters and leaves the "immersion cell".

Though this method would appear to be an exact "dry" equivalent of the fluid immersion method, it does have one serious disadvantage which makes it very difficult to apply in practice. In the fluid immersion method, the effect of gravity ensures that the light enters and leaves the immersion cell at the same angle, ideally at normal incidence, and thus symmetrically centered with respect to the lens under test. With the above prior art method of using two soft plastic pads, there exists a serious problem to ensure centralization and symmetry of the optical path through the "immersion cell" since the outer rigid surfaces of the pads cannot be kept accurately parallel. When the pads are forced into contact with the lens surface by means of mechanical pressure, there is a tendency for them to skew or shear sideways. In the above mentioned patent, jigs are used to try to ensure maintenance of centralization, but even this is not completely effective since even if the top and bottom rigid surfaces are constrained to be normal to the beam direction, the lens itself is supported only by the soft pliable plastic pads, and is thus free to move both axially and angularly. Once axial symmetry is lost, the measurement rays passing through the lens-pad assembly are no longer paraxial, therefore introducing aberrations and measurement inaccuracies.

There is another serious disadvantage of the double-sided method using pads with flat outer surfaces, as described in the above cited prior art. The described method and apparatus cannot be used in such cases where the combination of the flexible pad and the lens have zero power, since the sensitivity of the measurement is then zero.

Likewise, with lenses of very low power, the sensitivity is very low, and the resulting measurement inaccurate. Thus, despite its apparent simplicity, this method has not found acceptance in the ophthalmic industry, possibly because of the above mentioned problems in use.

Most of the above mentioned methods are time consuming, or require the use of expensive instrumentation, or are inconvenient to apply, especially those involving immersion of the lens in a fluid bath. The last described method, using two soft flexible plastic pads, though convenient and simple, suffers from an accuracy problem, which has not been solved in practice. There therefore exists a serious need for an instrument for measuring the refractive index of a lens, which is of low cost, enabling it to be widely used in ophthalmic practices, and which is convenient and speedy to use.

SUMMARY OF THE INVENTION

The present invention seeks to provide a new apparatus and method for measuring the refractive index of a lens. There is thus provided, in accordance with a preferred embodiment of the present invention, a thin insert in the form of a pad made of a flexible transparent material such as a polymeric material, one surface of the pad being provided with a rigid transparent cover, such as a thin glass sheet. The pad is lightly pressed onto a surface of the lens under test, such that the pad surface effectively acquires the same profile as the lens surface. The focal length or power of the lens is first measured without the insert, in a focimeter or a power meter. The measurement is then repeated with the insert positioned first in contact with one surface of the lens, and then in contact with the other surface. The use of equations adapted from the lens formula (1) then enables the refractive index of the lens to be easily and quickly determined. If an automatic lens power meter is used for the measurement, the calculation can be programmed into the instrument software, so that the result of the refractive index measurement be displayed directly. The use of a single insert avoids the problem of ensuring centralization which arises with the prior art method of using two inserts.

In accordance with another preferred embodiment of the present invention, there is provided a thin insert as described hereinabove, but wherein the rigid transparent cover sheet does not have flat surfaces, as in the Vieweg patent quoted above, but has a predetermined curvature. As a result of this curvature, it is possible to compensate for the situation of low power lenses under test, or the situation of a zero power lens/pad combination, by the addition of the power due to the predetermined curvature of the rigid sheet. However, use of the double-sided pad geometry according to the Vieweg prior art, with curved support sheets, results in a set of equations with more unknowns than available equations, and it is therefore impossible to extract the value of the unknown refractive index of the lens. On the other hand, the use of the single-sided geometry according to the present invention does allow a solution to be obtained, and therefore, unlike the Vieweg prior art, allows the measurement of refractive index to be performed for low power lenses and lens/pad combinations.

In accordance with another preferred embodiment of the present invention, there is provided a method of measuring the refractive index of a lens, consisting of the measurement of the power or the focal length of the lens in a suitable power or focal length meter, firstly without the use of a flexible insert pad, and then successively with the pad in contact with each surface of the lens.

The apparatus and method of the present invention is especially suitable for use with ophthalmic lenses. Furthermore, if the insert is produced of sufficiently soft material, it can even be used for measuring the refractive index of soft contact lenses.

In accordance with yet another preferred embodiment of the present invention, there is provided a refractometer for determining the refractive index of a lens, and consisting of a source for projecting a beam of light through the lens, a sheet of rigid transparent material disposed in the path of the light beam, close to a surface of the lens, a flexible transparent material of known refractive index, disposed such that it substantially fills the space between a surface of the lens and the sheet, and apparatus for determining the power of the combination of the lens, the sheet of rigid transparent material, and the flexible transparent material.

In accordance with a further preferred embodiment of the present invention, there is further provided a refractometer for determining the refractive index of a lens as described above and wherein the flexible transparent material of known refractive index, disposed such that it substantially fills the space between a surface of the lens and the sheet, consists of a pad of flexible transparent material attached to the sheet.

In accordance with still another preferred embodiment of the present invention, there is provided a refractometer for determining the refractive index of a lens as described above and wherein the surface of the pad of flexible transparent material which is not attached to the sheet, is in contact with a surface of the lens, such that it essentially acquires the curvature of the surface of the lens.

There is further provided in accordance with yet another preferred embodiment of the present invention a refractometer for determining the refractive index of a lens as described above and wherein the flexible transparent material of known refractive index, disposed such that it substantially fills the space between the surface of the lens and the sheet, is a fluid.

There is further provided in accordance with still another preferred embodiment of the present invention, a refractometer for determining the refractive index of a lens as described above, and wherein the fluid is contained in a bag, or is sufficiently viscous that it does not need to be contained in a bag.

There is provided in accordance with still a further preferred embodiment of the present invention, a refractometer for determining the refractive index of a lens as described above, and also consisting of an electronic control unit, the electronic control unit being operative to process the output of the apparatus for determining the power of the combination of the lens, the sheet of rigid transparent material, and the flexible transparent material, and to calculate and display the refractive index of the lens.

Furthermore, in accordance with yet another preferred embodiment of the present invention, there is provided a refractometer for determining the refractive index of a lens, and consisting of a source for projecting a beam of light through the lens, an insert constructed of a pad of flexible transparent material of known refractive index with a sheet of rigid transparent material attached thereto, the insert being disposed in contact with a surface of the lens, such that surface of the pad not attached to the sheet essentially acquires the curvature of the surface of the lens, and apparatus for determining the power of the combination of the lens and the insert in contact with a surface of the lens.

There is even further provided in accordance with a preferred embodiment of the present invention, a refractometer for determining the refractive index of a lens as described above, and consisting of also an electronic control unit, the electronic control unit being operative to process the output of the apparatus for determining the power of the combination of the lens and the insert, and to calculate and display the refractive index of the lens.

There is also provided in accordance with a further preferred embodiment of the present invention, a refractometer for determining the refractive index of a lens as described above, and wherein the flexible transparent material of known refractive index is an RTV silicone material.

In accordance with yet another preferred embodiment of the present invention, there is provided a refractometer for determining the refractive index of a lens as described above and wherein the rigid transparent material is glass.

In accordance with a further preferred embodiment of the present invention, there is further provided a refractometer for determining the refractive index of a lens as described above, and wherein the sheet of rigid transparent material can be either essentially flat or curved.

In accordance with still another preferred embodiment of the present invention, there is provided an insert consisting of a pad of flexible transparent material of known refractive index, with a sheet of rigid transparent material attached thereto, operative for determining the refractive index of a lens by disposing one such insert in contact with a surface of the lens, such that the surface of the pad of flexible transparent material is maintained in close contact with the lens surface by means of light applied pressure, and by determining the change in the power of the combination of the lens and the insert, with and without the insert.

There is further provided in accordance with yet another preferred embodiment of the present invention, an insert as described above, and wherein the sheet of rigid transparent material is curved.

There is provided in accordance with still a further preferred embodiment of the present invention, a method for determining the refractive index of a lens, consisting of the steps of transmitting a beam of light through the lens and determining the power of the lens, followed by the step of applying an insert constructed of a pad of flexible transparent material of known refractive index, with a sheet of rigid transparent material attached thereto, to one surface of the lens, with the pad of flexible transparent material maintained in close contact with the lens by means of light applied pressure, determining the power of the combination of the lens and the insert, thereafter applying the pad to the opposite surface of the lens and again determining the power of the combination of the lens and the insert, and finally calculating the value of the refractive index of the lens by means of derivations of the lens equation.

BRIEF DESCRIPTION OF THE DRAWINGS

The present invention will be understood and appreciated more fully from the following detailed description, taken in conjunction with the drawings in which:

In FIG. 1A, the sheet is flat, while in FIG. 1B it is curved;

FIGS. 3A and 3B show how the lens refractometer is set up using the insert shown in FIG. 2, to determine the refractive index of the lens under test, showing the geometry of the measurement. FIG. 3A shows the measurement without the insert, FIG. 3B with the insert in contact with one surface of the lens, and FIG. 3C with the insert in contact with the other surface;

DETAILED DESCRIPTIONS OF PREFERRED EMBODIMENTS

Figure 1A:
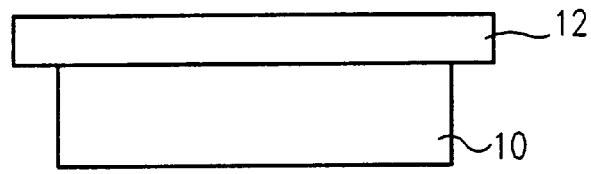
FIG. 1A and FIG. 1B are drawings of flexible inserts according to preferred embodiments of the present invention, each insert being constructed of a pad of flexible transparent material bonded to a transparent sheet.
Figure 1B:

Reference is now made to FIGS. 1A and 1B, each of which illustrate a flexible insert, as used in a lens refractometer constructed and operative according to a preferred embodiment of the present invention. The inserts are preferably constructed of a thin pad of transparent flexible material 10, preferably of lateral dimensions somewhat smaller than the diameter of the lens to be tested. The thickness is typically at least twice the sagittal distance of the lens under test. On one surface of the insert is preferably attached a rigid sheet of transparent material, such as a glass microscope slide or a section of stiff plastic sheet. FIG. 1A shows such an insert with a flat sheet of transparent material 12, while FIG. 1B shows a similar insert with a sheet of transparent material 13 with a predetermined curvature, which can be spherical or aspherical. The use of a curved sheet instead of a flat sheet, allows the addition of power to the lens pad assembly, so that low power lenses can be measured.

Figure 2:
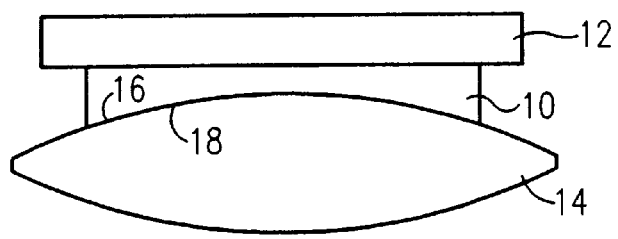
FIG. 2 is a drawing of the insert of FIG. 1A applied to a lens under test.

FIG. 2 shows how the insert illustrated in FIG. 1A is disposed on a surface 18 of the lens under test 14. It is held in intimate contact therewith by means of slight pressure, so that the bottom surface 16 of the flexible pad 10 conforms to the profile of the top surface 18 of the lens, substantially to the exclusion of any air space.

FIGS. 3A, 3B and 3C show how the lens refractometer is used in conjunction with a focimetric or lens power measurement, to determine the refractive index of the lens under test, according to another preferred embodiment of the present invention. In FIG. 3A the instrument is shown performing a measurement of the focal length of the lens under test 20, having a refractive index n. One surface 24 of the lens has a radius of curvature $r_1$, and the other surface 26, a radius of curvature $r_2$. A collimated input beam of light 22 passes through the lens, and is brought to a focus at its effective focal length $f_1$. Applying the lens equation to this case, the following formula for $f_1$ is obtained in terms of the unknowns n, $r_1$ and $r_2$:

$$1/f_1 = (n-1)[1r_1 - 1/r_2] \tag{3}$$

FIG. 3B shows the lens refractometer according to the present invention, with a second focimetric measurement being made while the lens 20 is mounted in the test position, with insert 30 in close contact with its top surface, and substantially without any air spaces intervening. The refractive index of the flexible pad 34 of the insert has a known value $n_1$. The insert is positioned such that the input beam of light 38 is incident on the flat top surface plate 40 of the insert at normal incidence.

If the lens/pad combination is viewed as a doublet composed of two thin lens, then the total power of the doublet is equal to the sum of the power of its two components separately. Taking the pad alone as one of the lenses of the doublet, the focal length $f_{PI}$ for this "pad lens" is given by:

$$1/f_{P1} = (n_1 - 1)[1/r_1] \tag{4}$$

where $n_1$ is the refractive index of the pad, as previously. Since the top surface of the pad is flat, its top surface radius of curvature is infinite.

For the "lens only" part of the doublet, the focal length $f_1$ is given by equation (3). The power of the complete doublet $1/f_{D1}$, with the pad on surface 1, is therefore given by the sum of equations (3) and (4), as follows:

$$1/f_{D1}=(n-1)\,[1/r_1 1/r_2]+(n_1-1)\,[1/r_1] \qquad (5)$$

If the lens under test is a planar-convex lens, then $1/r_2=0$, and the solution of equations (3) and (5) enable the unknown refractive index n to be determined.

For the more general case, however, an additional equation is required to solve for n, and this is obtained by making an additional power measurement with the pad on the bottom surface of the lens, whose radius of curvature is $r_2$. This is shown in FIG. 3C. If the lens/pad doublet calculation is repeated for this case, the power of the complete doublet $1/f_{D2}$, with the pad on surface 2, is given by:

$$1/f_{D2}=(n-1)\,[1/r_1-1/r_2]-(n_1-1)\,[1/r_2] \qquad (6)$$

Simultaneous solution of equations (3), (5) and (6), arising from the three power measurements made, thus enables the refractive index n of the lens to be calculated. Though the above equations have been derived for the case of an incident collimated beam of light, the calculations can also be performed for the more general case of a non-collimated incident beam.

Though the above equations have been derived for the case of a flat rigid sheet as the outer surface of the pad, similar equations can be derived for the case of a curved sheet. It can be shown by those familiar with the art that, by using a single pad with a curved sheet alternately on both surfaces of the lens under test, a solution for the unknown lens refractive index can be obtained, unlike the case for the double pad applied on both sides of the lens. This embodiment therefore also enables low power lenses to be tested, as well as lens/pad combinations which have low powers.

If the measurement is being made on an automated power meter, equations (3), (5) and (6) and the fixed value of $n_1$ can be incorporated into the measurement software of the refractometer, such that it is only necessary to input the two measured focal distances $f_1$ and $f_2$ for the lens under test, by means of a simple mouse or keyboard operation, and the instrument will perform the calculation and output the unknown required refractive index. According to another preferred embodiment of the present invention, the values of the focal distances $f_1$ and $f_2$ can be inputted automatically to the instrument control system by position encoders for inputting electronic signals representing these focal positions.

The thin pads of transparent flexible material, according to a preferred embodiment of the present invention, are made of transparent RTV, but any suitable flexible plastic or polymeric material may be successfully used. The flexibility of the material must be chosen such that under the pressure required to maintain the insert in good contact with the lens surface, the lens does not undergo any deformation which would affect its focusing power. Thus, for glass lenses, a fairly stiff pad may be used, while for plastic lenses, a more flexible pad would be suitable, and for soft contact lenses, a very flexible pad would be required. In general, the use of softer pads provides the most universal coverage of lens types, but the softer the pad, the quicker is it likely to be worn out. The transparent plate on top of the pad must be sufficiently rigid that it maintains its optical form under the pressure applied to the pad.

The refractive index $n_1$ of suitable transparent RTV samples from which the flexible pad may be composed is preferably in the range of approximately 1.33 to 1.43. These values are close to the refractive index of many optical glasses, which range from about 1.5 to 1.9. Many of the other suitable plastics for use as pad material also have refractive indexes in this region. The use of pad materials such as these, with refractive index close to that of the lens under test, such that $(n-n_1)$ is small, increases the sensitivity and accuracy of the measurement. This is self evident from the simple immersion case whose result is given in equation (2), and can also be shown by one familiar with the art, to follow from the algebra of equations (3), (5) and (6).

Figure 4:
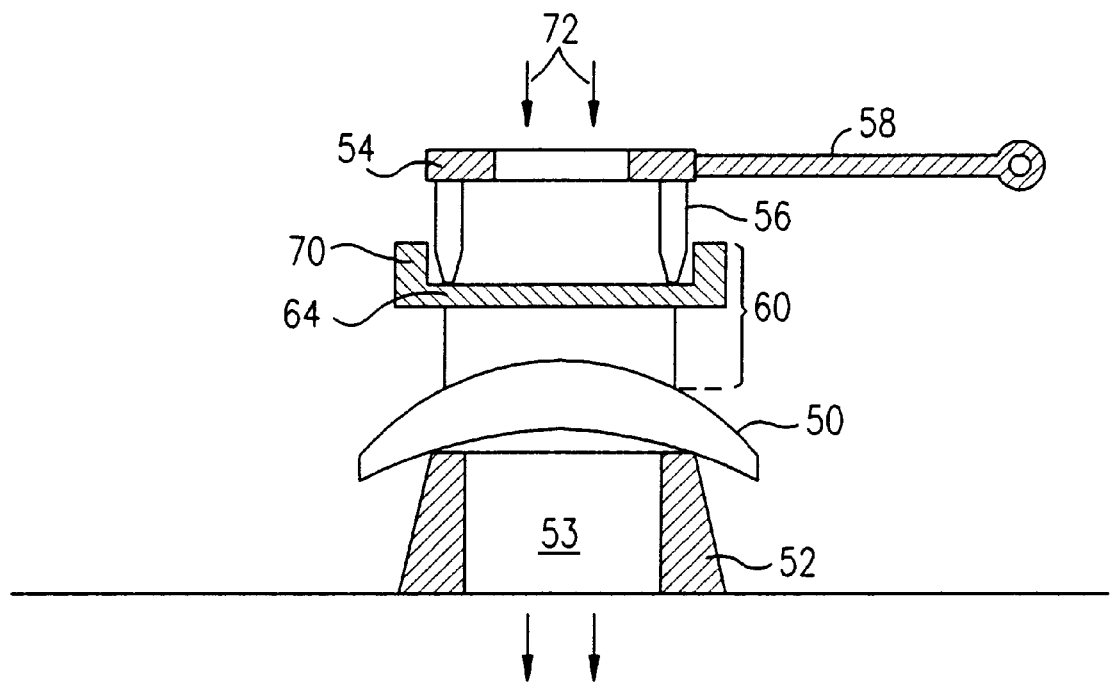
In FIG. 4 depicted a schematic view of a complete refractometer according to a preferred embodiment of the present invention.

FIG. 4 shows a refractometer, constructed and operative according to a preferred embodiment of the present invention, mounted on a lens power meter, to illustrate how the pad insert and the lens are aligned both relative to each other, and with respect to the illuminating beam and measuring system. During a power measurement, the lens under test 50 is aligned perpendicular to the incident beam 72 by means of a circular support ring 52, through whose hollow center 53 the measuring beam passes after being refracted by the lens. The lens is generally held in position by a blocker 54, which has a number of feet 56 which gently keep slight pressure on the lens to ensure its positive seating on the support ring 52. The blocking mechanism is generally dropped or swung into place by means of its support arm 58.

When the blocking mechanism descends onto the lens, the pad insert 60 is firmly held in its correct position. The slight pressure exerted by the blocking mechanism ensures that the flexible pad material is compressed into contact with the lens surface. When making the measurement with the insert on top of the lens, the flat transparent plate 64 of the insert is constrained to sit perpendicular to the incident beam because of its contact with the feet 56 of the blocking mechanism. When the measurement is performed with the insert on the bottom of the lens, contact of the flat transparent plate with the lip of the support ring 52 ensures perpendicularity. The flat end plate 64 of the pad insert can be equipped with a locating ring 70 to ensure that it is correctly centered in its designated position.

The above embodiments have been described with pads constructed of flexible solid materials. It is appreciated, however, that the scope of this invention is not limited to such solid pads, but that it is possible to use any material which conforms to the lens surface profile under light pressure. Thus, for instance, thin walled bags or balloons filled with liquids of suitable refractive index can also be used as the pad material, sandwiched between the transparent plate and the lens. Suitable fluids for this purpose include, for instance, water, glycerin, silicone oils, and others.

Figure 5:
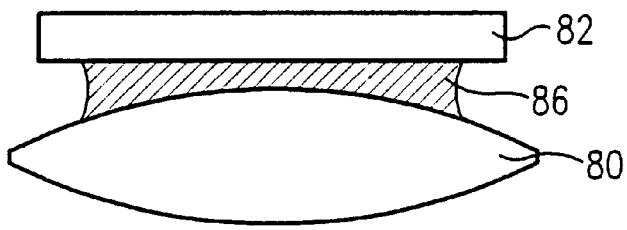
FIG. 5 shows how a viscous fluid or grease can be used instead of the flexible transparent pad used in the insert shown in FIG. 2.

In a similar manner, according to a further embodiment of the present invention, if the fluid is sufficiently viscous, there is no need to employ a bag to contain it. This embodiment is shown in FIG. 5, where the lens 80 is almost in contact with a transparent flat plate 82, and the intervening space 86 filled with the viscous fluid of known refractive index. Suitable fluids are greases and viscous silicone oils. This embodiment has the disadvantage that the lens under test has to be cleaned after the measurement, this being one of the disadvantages of some of the prior art methods mentioned hereinabove.

It is also appreciated that though the above embodiments have been described using convex or plano-convex lenses for the lenses under test, the present invention can equally be used for any other types of lenses such as concave lenses, plano-concave lenses, meniscus lenses, aspheric lenses, multi-focal progressive lenses, toric lenses, and others. In lenses having different powers in different axes, such as toric or progressive lenses, it is important to maintain the same location and orientation of the lens for the power measurements with and without the pad inserts, in order to obtain accurate results.

There is further provided, in accordance with another preferred embodiment of the present invention, a method of measuring the refractive index of a lens, comprising firstly the step of transmitting a beam of light through the lens and determining the focal position of the beam after traversing the lens. This is followed by the step of applying to one surface of the lens, a flexible transparent pad with a transparent sheet bonded onto one of its surfaces, with the flexible pad maintained in close contact with the lens by means of light applied pressure. The focal position of the beam after traversing the lens is again determined. Then, the procedure is repeated with the pad applied to the opposite surface of the lens. Finally, the value of the refractive index of the lens is calculated by means of equations (3), (5) and (6) if the transparent sheet bonded to the pad is a flat sheet, or by means of other equations similarly derived from the lens equation if the transparent sheet is curved.

It will be appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

I claim:

1. A refractometer for determining the refractive index of a lens, and comprising:
    a source for projecting a bean of light through said lens;
    a sheet of rigid transparent material disposed in the path of said light beam, coaxially with said lens and close to a surface of said lens;
    a flexible transparent material of known refractive index, disposed such that it substantially fills the space between said surface of said lens and said sheet; and
    a power meter for determining the power of said lens, and of a combination of said lens with only a single one of said sheet of rigid transparent material and said flexible transparent material.

2. A refractometer for determining the refractive index of a lens according to claim 1 and wherein said flexible transparent material of known refractive index, disposed such that it substantially fills the space between said surface of said lens and said sheet, comprises a pad of flexible transparent material having a first and second surface, attached to said sheet at its first surface.

3. A refractometer for determining the refractive index of a lens according to claim 2 and wherein said second surface of said pad of flexible transparent material is in contact with a surface of said lens, such that said second surface of said pad essentially acquires the curvature of said surface of said lens.

4. A refractometer for determining the refractive index of a lens according to claim 1 and wherein said flexible transparent material of known refractive index, disposed such that it substantially fills the space between said surface of said lens and said sheet, is a fluid.

5. A refractometer for determining the refractive index of a lens according to claim 4, and wherein said fluid is contained in a bag.

6. A refractometer for determining the refractive index of a lens according to claim 4, and wherein said fluid is sufficiently viscous that it does not need to be contained in a bag.

7. A refractometer for determining the refractive index of a lens according to claim 1, and also comprising an electronic control unit, said electronic control unit being operative to process the output of said power meter for determining the power of said lens, and of a combination of said lens with only a single one of said sheet of rigid transparent material and said flexible transparent material, and to calculate said refractive index of said lens.

8. A refractometer for determining the refractive index of a lens, and comprising:
    a source for projecting a beam of light through said lens;
    a single insert comprising a pad of flexible transparent material of known refractive index, said pad having a first and a second surface, with a sheet of rigid transparent material attached to said first surface of said pad, said insert being disposed in contact with one surface of said lens, such that said second surface of said pad essentially acquires the curvature of said surface of said lens; and
    a power meter for determining the power of said lens and of a combination of said lens and said single insert in contact with a surface of said lens.

9. A refractometer for determining the reactive index of a lens according to claim 8, and comprising also an electronic control unit, said electronic control unit being operative to process the output of said power meter for determining the power of said lens and of a combination of said lens and said single insert, and to calculate and display said refractive index of said lens.

10. A refractometer for determining the refractive index of a lens according to claim 1, and wherein said flexible transparent material of known refractive index is an RTV silicone material.

11. A refractometer for determining the refractive index of a lens according to claim 1, and wherein said rigid transparent material is glass.

12. A refractometer for determining the refractive index of a lens according to claim 1, and wherein said sheet of rigid transparent material is essentially flat.

13. A refractometer for determining the refractive index of a lens according to claim 1, and wherein said sheet of rigid transparent material is curved.

14. A refractometer for determining the refractive index of a lens according to claim 8, and wherein said sheet of rigid transparent material is essentially flat.

15. A refractometer for determining the refractive index of a lens according to claim 8, and wherein said sheet of rigid transparent material is curved.

16. An insert comprising a pad of flexible transparent material of known refractive index, with a sheet of rigid transparent material attached thereto, operative for determining the refractive index of a lens by disposing said insert in contact with a surface of said lens, such that a surface of said pad of flexible transparent material is maintained in close contact with a surface of said lens by means of light applied pressure, and by determining the change in the power of said lens when measured in combination with a single one of said insert.

17. An insert according to claim 16, and wherein said sheet of rigid transparent material is curved.

18. An insert according to claim 16, and wherein said sheet of rigid transparent material is flat.

19. A method for determining the refractive index of a lens having first and second surfaces, comprising the steps of:
    transmitting a beam of light through said lens and making a first power measurement of said lens;

enveloping at least part of said first surface only with a flexible transparent material of known refractive index and making a second power measurement;

enveloping at least part of said second surface only with a flexible transparent material of known refractive index and making a third power measurement; and using said three power measurements to computer said refractive index of said lens.

20. The method according to claim 19 and wherein said steps of enveloping at least part of said surface are performed by applying to said surface an insert constructed of a pad of flexible transparent material of known refractive index, with a sheet of rigid transparent material in contact therewith.

21. A method for determining the refractive index of a lens according to claim 19, and also comprising the step of maintaining said pad of flexible transparent material of said insert in close contact with a surface of said lens by means of light applied pressure.

* * * * *